(12) United States Patent
Saadon

(10) Patent No.: US 11,045,333 B2
(45) Date of Patent: Jun. 29, 2021

(54) PROSTHETIC HOOK ADAPTOR FOR SPORTING EQUIPMENT

(71) Applicant: Marschell B. Saadon, Killeen, TX (US)

(72) Inventor: Marschell B. Saadon, Killeen, TX (US)

(73) Assignee: LIFEWORK ADAPTER LLC, Austin, TX (US)

( * ) Notice: Subject to any disclaimer, the term of this patent is extended or adjusted under 35 U.S.C. 154(b) by 45 days.

(21) Appl. No.: 16/543,488

(22) Filed: Aug. 16, 2019

(65) Prior Publication Data
US 2020/0138603 A1  May 7, 2020

Related U.S. Application Data

(60) Provisional application No. 62/764,973, filed on Aug. 16, 2018.

(51) Int. Cl.
*A61F 4/00* (2006.01)
*A61F 2/58* (2006.01)

(52) U.S. Cl.
CPC .................................. *A61F 2/588* (2013.01)

(58) Field of Classification Search
CPC .... A61F 2/588; A61F 4/00; A61F 2002/5083; A61F 2/76; A61F 2/54; A61F 2/583; A61F 2/585; A61F 2/586; A61F 2/58; A61F 2/78; A61F 2002/543; A61F 2002/587; A61F 2/50; F41G 3/165; F41C 23/20; F41C 23/16; F41C 27/00
See application file for complete search history.

(56) References Cited

U.S. PATENT DOCUMENTS

| | | | | |
|---|---|---|---|---|
| 4,159,545 | A | * | 7/1979 | Manning ................. A61F 2/588 623/65 |
| 5,271,555 | A | * | 12/1993 | Mayer .............. A47G 29/12097 232/17 |
| 2019/0283061 | A1 | * | 9/2019 | Qiao ..................... B05B 9/0861 |
| 2020/0393208 | A1 | * | 12/2020 | Barrett ..................... F41A 3/66 |

* cited by examiner

*Primary Examiner* — Jennifer Dieterle
*Assistant Examiner* — Mihret Tafesse

(57) ABSTRACT

A prosthetic adaptor includes a post plate, a grip plate coupled to the post plate, and an equipment interface coupled to the post plate. The equipment interface can be coupled to the post plate at an end of the post plate distal from the grip plate. The post plate can include a concave surface. The concave surface can be configured to receive a Hosmer-like prosthetic hook.

19 Claims, 11 Drawing Sheets

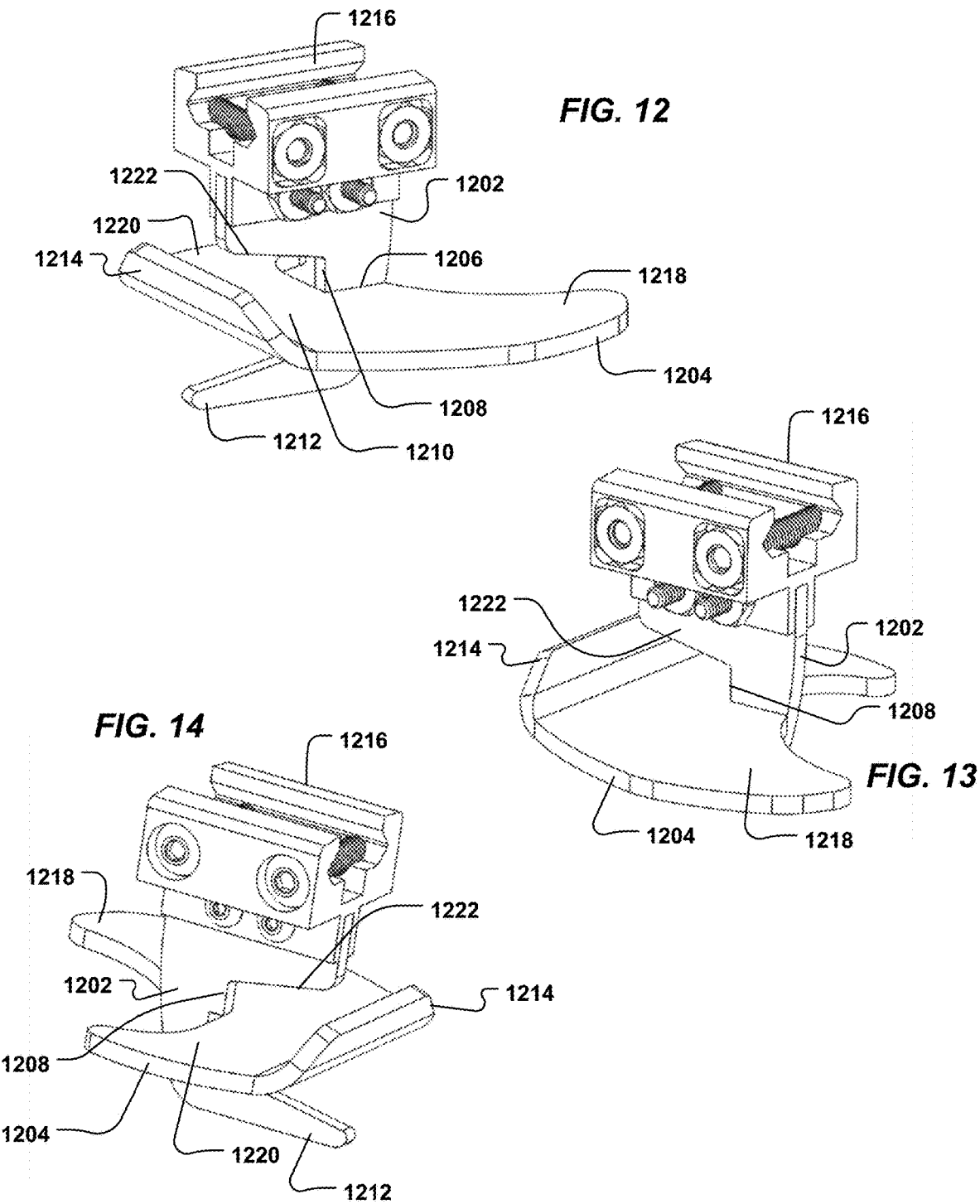

PROSTHETIC HOOK ADAPTOR FOR SPORTING EQUIPMENT

CROSS-REFERENCE TO RELATED APPLICATION(S)

This application claims benefit of U.S. Provisional Application No. 62/764,973, filed Aug. 16, 2018, which is incorporated herein by reference in its entirety.

FIELD OF THE DISCLOSURE

This disclosure, in general, relates to an adapter for sporting equipment for prosthetic hooks.

BACKGROUND

As a result of global military conflicts, industrial accidents, and automobile or sporting accidents, a large number of individuals have lost a portion of a hand or a section of an arm. While various prosthetic devices have been created as a replacement for a lost appendage, the 2-part prosthetic hook remains a dominant prosthetic in the marketplace. But, it has its limitations. As such, amputees are often left without the ability to participate in sports or are required to use inconvenient adapters in place of the prosthetic hook. Moreover, many amputees are limited in their ability to return to work, particularly where work has a physical requirement to use particular equipment, such as firearms for law enforcement officers.

BRIEF DESCRIPTION OF THE DRAWINGS

The present disclosure may be better understood, and its numerous features and advantages made apparent to those skilled in the art by referencing the accompanying drawings.

FIG. 12, FIG. 13, FIG. 14, FIG. 15, and FIG. 16 include illustrations of a further example adapter for sporting equipment.

The use of the same reference symbols in different drawings indicates similar or identical items.

DETAILED DESCRIPTION

In an embodiment, an adapter can be provided that permits prosthetic hooks to securely attached to sporting equipment and provide multidimensional control, such as multi-axis control and rotation, of sporting equipment using a prosthetic hook. Example prosthetic hooks include Hosmer-like hooks, such as hooks dimensioned similar to Hosmer 5 or Hosmer 7 prosthetic hooks. In a particular example, the adapter can be fitted to a firearm, such as a rifle or handgun. Alternative embodiments can be readily be envisioned based on the disclosure herein for adaptation to other sporting equipment including bows, weights, rackets, and bats, among others.

Figure 1:
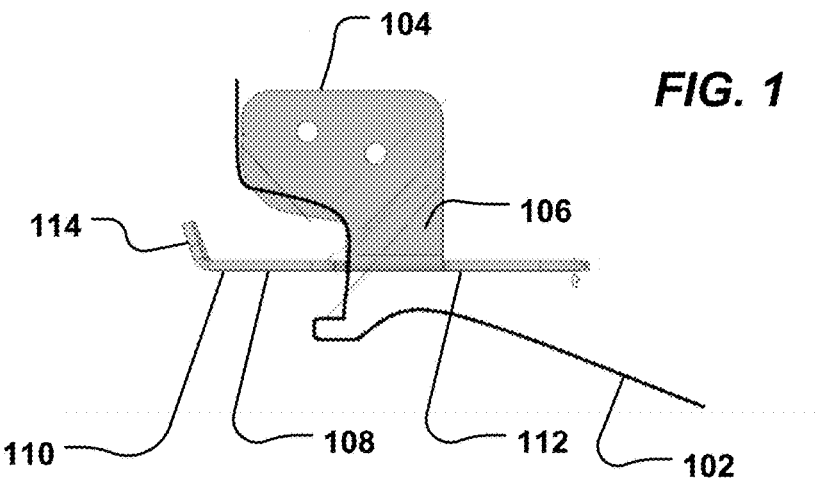
FIG. 1, FIG. 2, FIG. 3, FIG. 4, and FIG. 5 include illustrations of a prosthetic adapter to be used with an existing foregrip.
Figure 2:
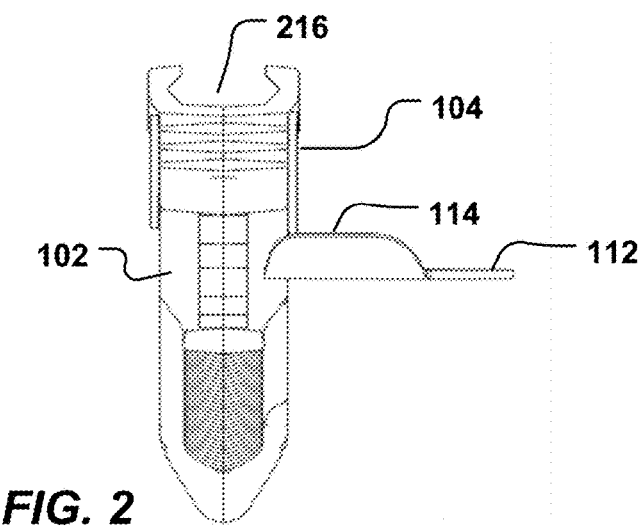

As illustrated in FIG. 1, an adapter to an existing foregrip of a firearm, such as a rifle or shotgun, can permit the griping of the foregrip with a prosthetic hook. For example, the foregrip 102 can be adapted with adapter 104 that includes a vertical plate portion 106 and a horizontal plate portion 108. The horizontal plate portion 108 can include a portion 112 that extends to the side of the foregrip 102 and a portion 110 that extends forward from the foregrip 102. In addition, the plate portion 108 can include a retention lip 114. As illustrated in FIG. 2, the grip 102 can include an attachment section 216 that attaches to rails on the rifle or shotgun.

FIG. 2 additionally illustrates the extension of the plate portion 112 to the side of the grip 102. In use, the hook is extended or opened so that one side enters the capture port above the horizontal plate 108 at the forward extension 110 and the second part of the hook extends under the horizontal plate 108. Accordingly, the curved part of the hook wraps around the front of the foregrip 102. A back portion of the grip further grips the side extension 112. The hook is prevented from moving forward when closed by the retention lip 114. Although retention lip 114 is illustrated as extending upward, an additional retention lip may further be provided that extends downward.

Figure 3:
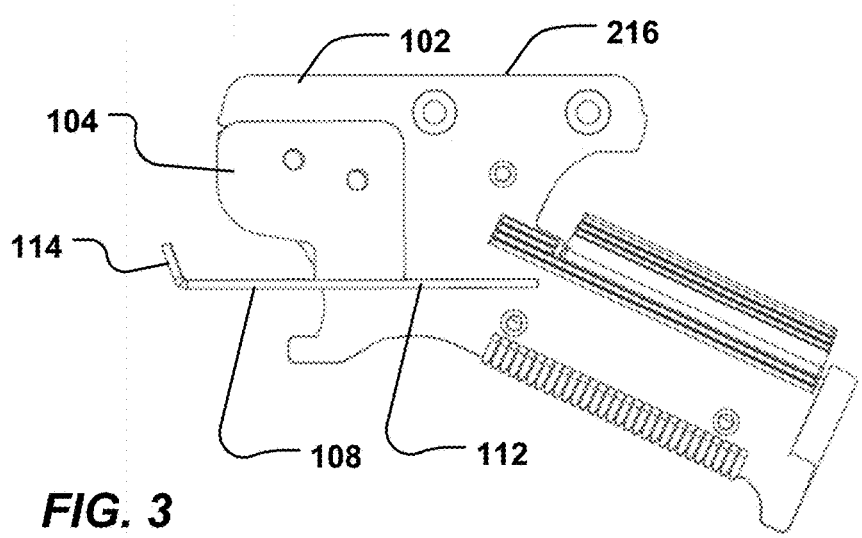
Figure 4:
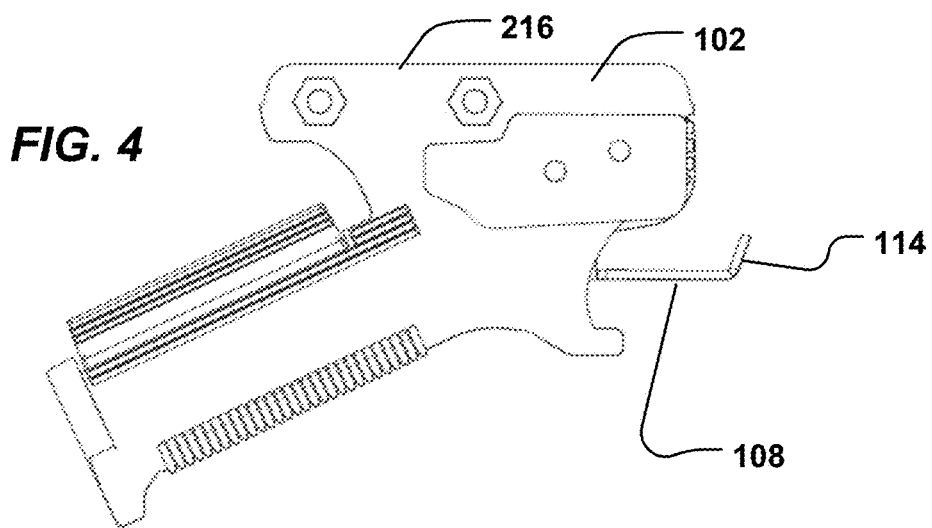
Figure 5:
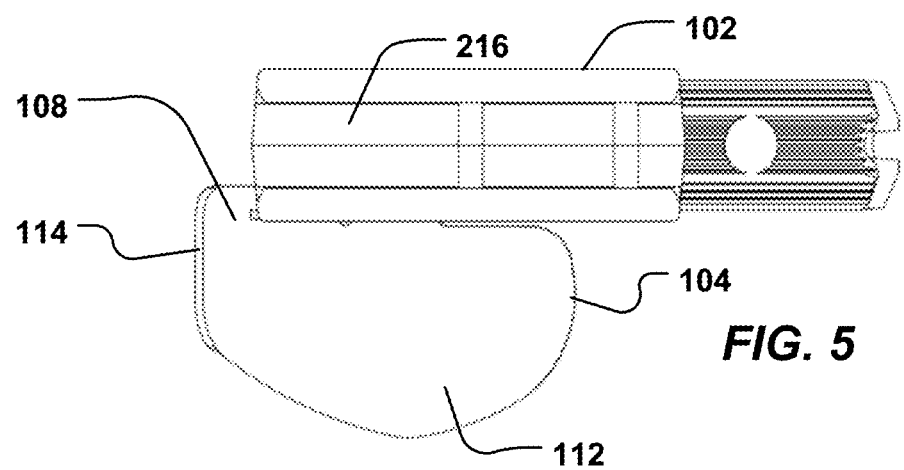
Figure 6:
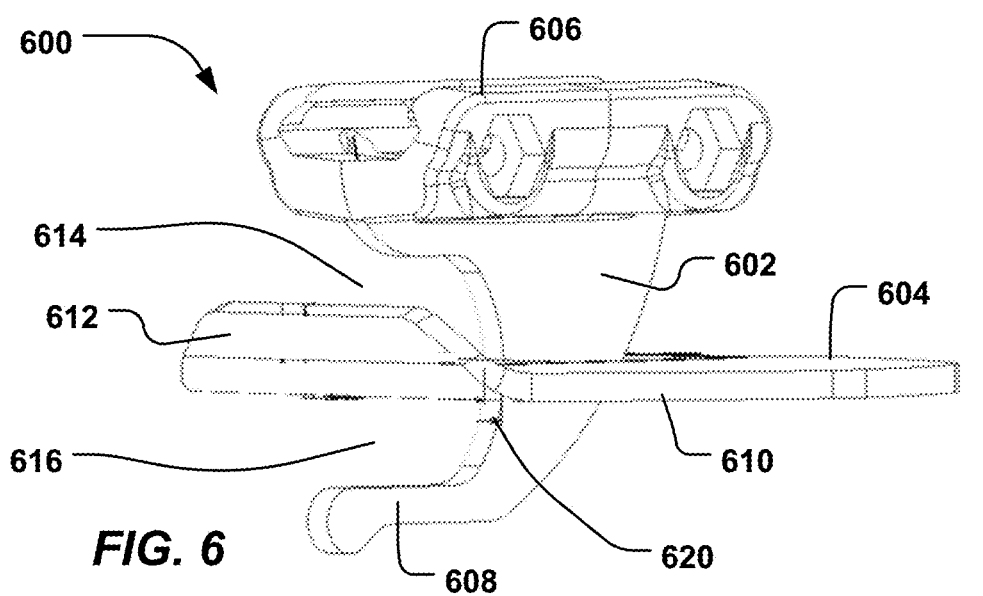
FIG. 6, FIG. 7, FIG. 8, FIG. 9, FIG. 10, and FIG. 11 include illustrations of an example adapter for sporting equipment.

The plates 106 and 108 can be formed of rigid polymer or metal materials. In addition, the surface of the horizontal plate 108 such as portion 110 or portion 112 can be coated with an elastomeric material to further secure the hook. FIG. 3, FIG. 4, and FIG. 5 illustrates additional views of the adapter 104.

FIG. 6, FIG. 7, FIG. 8, FIG. 9, FIG. 10, and FIG. 11 illustrates an adapter 600 to be used with various sporting equipment. The adapter 600 can include a central shaft or post plate 602 attached to a horizontal plate or grip plate 604. In addition, the adapter 600 can include a connector 606. The connector 606 can take various forms such that the connector can attach to sporting equipment. For example, the connector can connect to a Picatinny rail. In another example, the connector 606 can connect to an M Lok connector.

Horizontal plate 604 attached to the central shaft or plate 602 can extend sideways to one or both sides of the central shaft or plate 602. In addition, the horizontal plate 604 can include a lip 612 that extends forward of the central shaft or plate 602. In addition, the central shaft or plate 602 can extend below the horizontal plate 604 and form a space 616 enclosed on three sides by the extension of the shaft 608 and the horizontal plate 604. In addition, an opening or space 614 is defined between the lip 612 and the shaft or plate 602.

Figure 7:
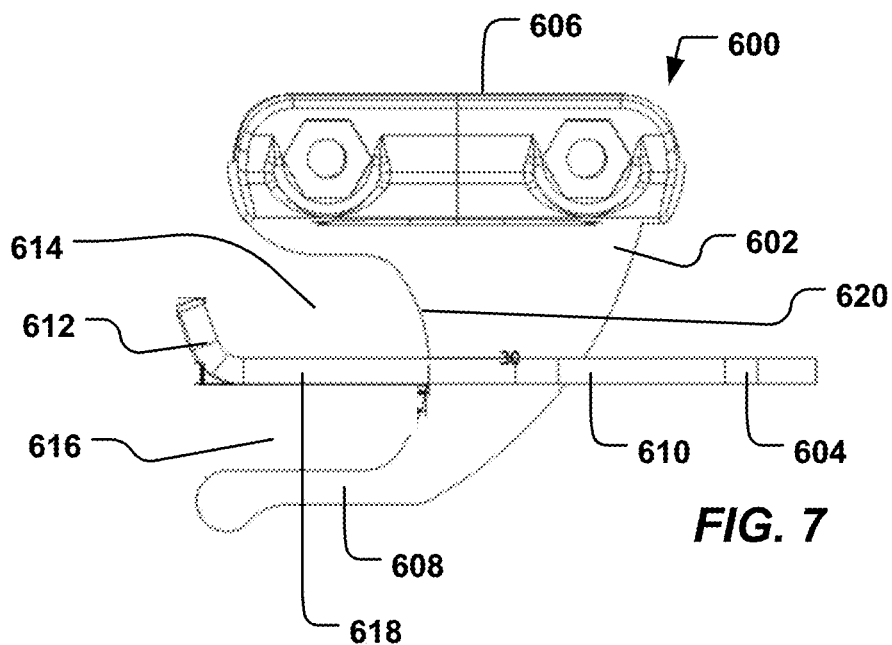
Figure 8:
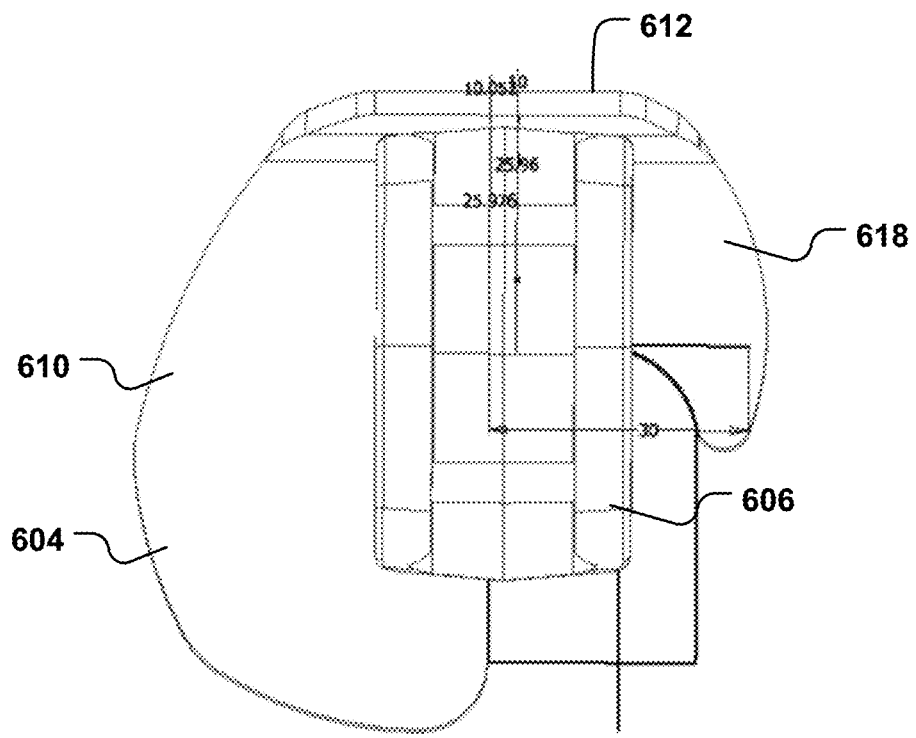
Figure 9:
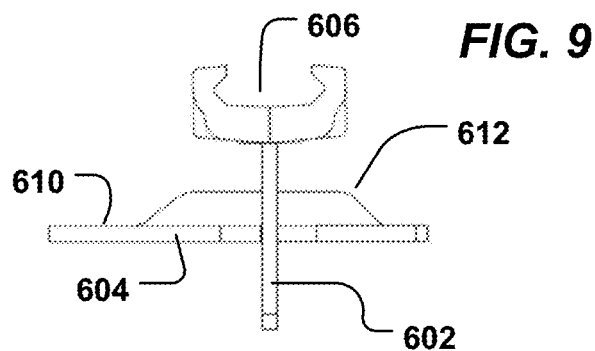
Figure 10:
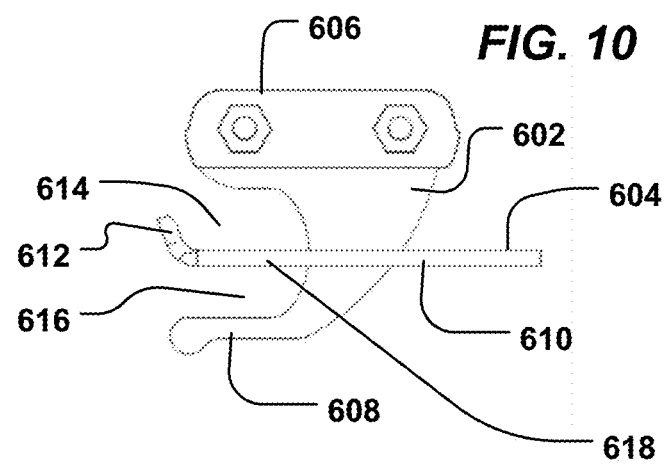
Figure 11:
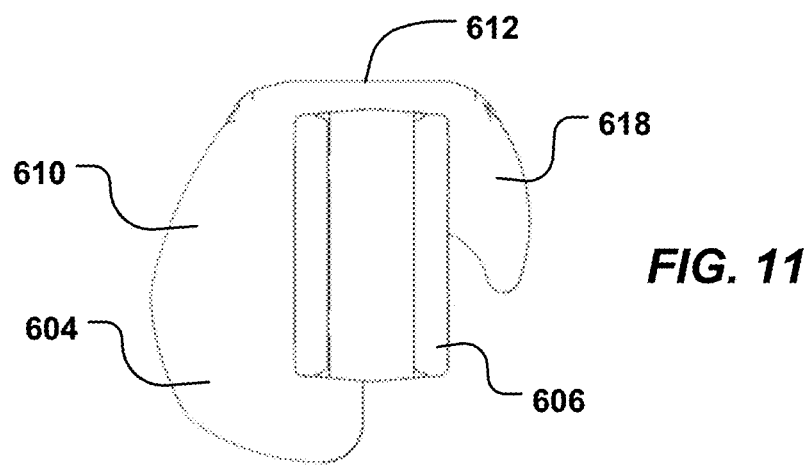

As illustrated in FIG. 7, the plate 604 further extends forward from the central shaft or plate 602 as illustrated at portion 618. In use, the curved portions of the hook can be placed above and below the forward extension 618 of the horizontal plate 604 and slide into open spaces 614 and 616. The hook is then close to around the horizontal plate 604, placing the forward curved portions over and under the forward extension 618 and part of the straight portion of the hook on the plate portion 610. When closed, the lip 612 prevents forward movement of the kooks. Optionally, a second lip can extend downward further assisting with securing the hook in place when it's closed. Further, the plate 602 can have a curved surface 620 that pinches the hook portions when they are drawn back toward the plate 602. Optionally, the horizontal plate 604 can be a metal plate. Optionally, the metal plate can be coated with an elastomeric material to assist with preventing slippage of the hook.

As illustrated in FIG. 12, FIG. 13, FIG. 14, FIG. 15, and FIG. 16, a post plate 1202 is coupled with a grip plate 1204. The adapter can further include a connector or equipment interface 1216 coupled to the post plate 1202. For example, the connector or equipment interface 1216 can be a Picatinny rail or an M Lok interface common in the firearms, Airsoft, or crossbow sports, among other markets.

The grip plate 1204 can be coupled to the post plate 1202 in an approximately perpendicular fashion. As used in herein, approximately perpendicular means closer to perpendicular than parallel. For example, the post plate 1202 can be coupled to the grip plate 1204 in a perpendicular manner. For example, when the post plate 1202 is vertical, the grip plate 1204 is horizontal. The post plate 1202 can coupled with the grip plate 1204 at location 1206. For example, post plate 1202 can be adhered to the grip plate 1204, welded to the grip plate 1204, or mechanically secured to the grip plate 1204.

The post plate 1202 can be formed of a sheet material, such as a sheet metal. Example metals include stainless steel, steel, aluminum, and titanium, among others. In another example, the post plate 1202 can be formed of a polymeric material. In a further example, the post plate 1202 can be placed replaced with a rod. Similarly, the grip plate 1204 can be formed of a sheet material, such as a sheet metal or a polymeric sheet, such as those described above.

That post plate 1202 includes a concave surface 1208 defining an upper ridge 1222 within the concave surface 1208 and a lower ridge 1212 within the concave surface 1208. The grip plate 1204 extends forward at 1210 from the concave surface 1208 of the post plate 1202.

The grip plate 1204 can further include a lip 1214 disposed at a front edge of the grip plate 1204 distal from the concave surface 1208. Optionally, lip 1214 can extend out of the plane defined by the grip plate 1204, for example, upward towards the equipment interface 1216. Alternatively, the lip 1204 can extend downward towards the lower ridge 1212.

The grip plate 1204 can extend further along one side of the post plate 1202 than along another side. For example, the side 1218 extends out and back from the post plate 1202, optionally extending further rearward than the post plate 1202. In contrast, an opposite side 1220 of the grip plate 1204 extends partially out and rearward to a lesser extent than the side 1218.

In use, a Hosmer-like prosthetic hook, for example a Hosmer 5 or Hosmer 7 prosthetic hook engages the adapter from the side that extends further out. For example, the Hosmer-like prosthetic hook can engage the side 1218, with a top finger of the hook extending over the grip plate 1204 along side 1218 and moving around to side 1220. The other finger can extend under the plate 1204 and around the post plate 1202. In particular, a top finger of the hook can reach around the post plate 1202 and engage the concave surface 1208 between the upper ridge 1222 and the grip plate 1204, while a second finger of the Hosmer-like hooked engages the adapter between the lower ridge 1212 and the grip plate 1204.

Figure 15:
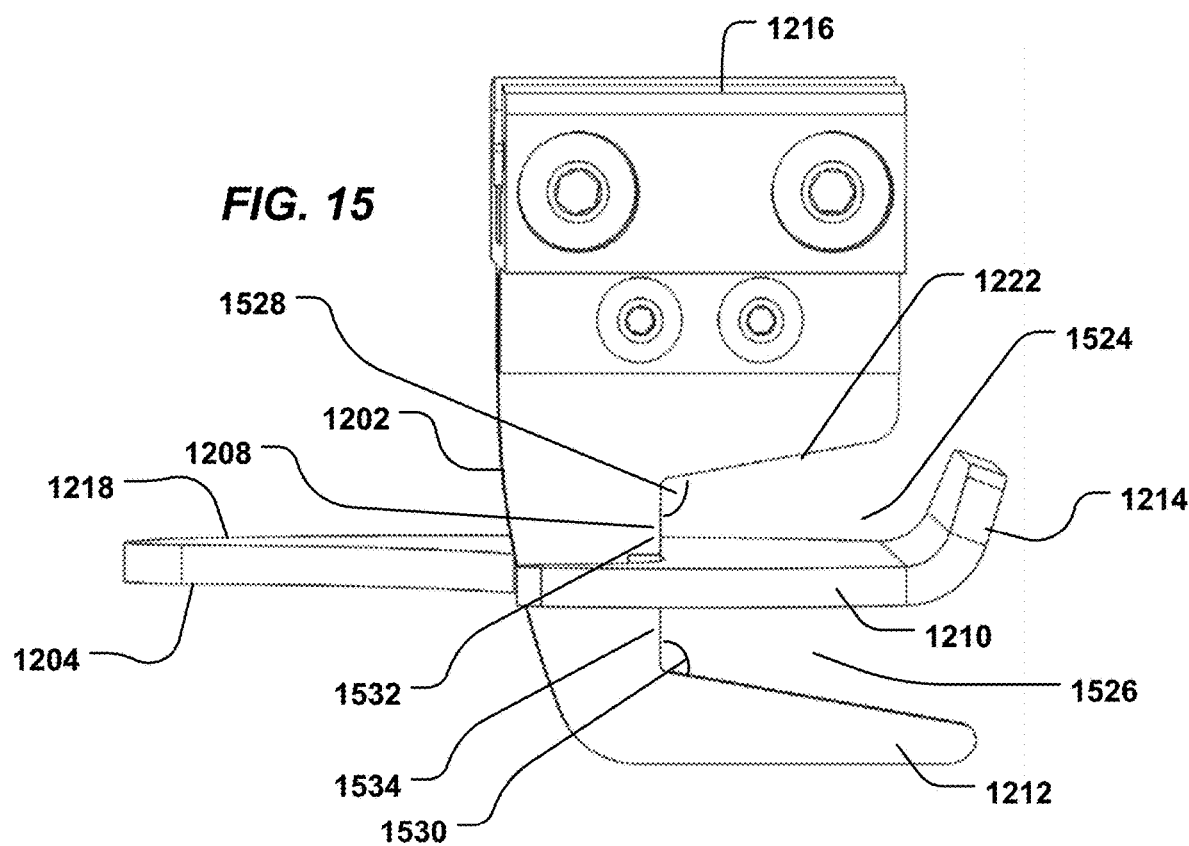
Figure 16:
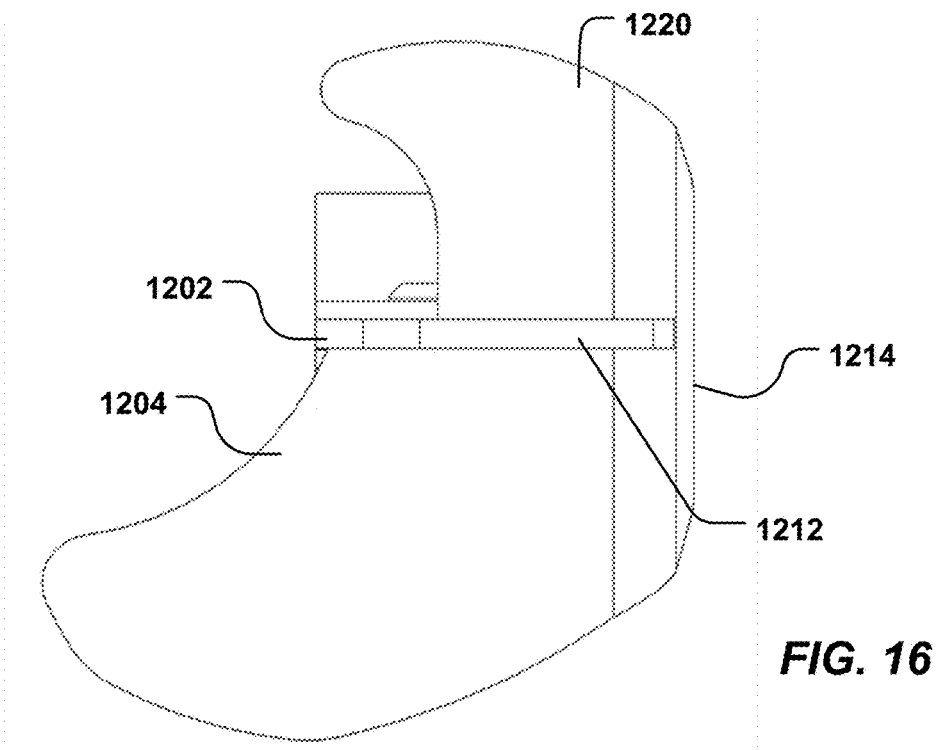

In particular, as illustrated in FIG. 15, the Hosmer-like prosthetic hook can reach around the post plate 1202 over and under the grip plate 1204 into cavities 1524 or 1526. For example, as a top finger of the Hosmer-like hook enters the cavity 1524 and is drawn rearward towards the concave surface 1208, the top finger engages the upper ridge 1222 of the post plate 1202 and the upper surface of the grip plate 1204. The upper ridge 1222 is either curved or joins at an angle relative to the rear surface 1532 of the concave surface 1208. Similarly, a lower finger of the Hosmer-like hook can enter into cavity 1526 and engage lower ridge 1212 and a surface of the grip plate 1204. The lower ridge 1212 is either curved or engages the rearward surface 1532 of the concave surface 1208 at an angle. As the fingers of the Hosmer-like hook are drawn rearward towards the rear surface 1532 of the concave surface 1208, the fingers of the Hosmer-like prosthetic hook are pinched in place. Often, the fingers include a resilient material that is compressed as the hook fingers are drawn into cavities 1524 or 1526.

In a particular example, the upper ridge 1222 can form an angle 1528 with the rear surface 1532 of the concave surface 1208. Similarly, the lower ridge 1212 can form an angle 1530 with rearward surface 1532. In an example, the angle is in a range of 90° to 130°, such as a range of 95° to 120° or even a range of 95° to 110°.

Further, an entrance to the cavity 1524 defined by the distance between the lip 1214 and the closest edge of the post plate 1202 can have a desirable width. For example, the width can be in a range of 0.15 inches to 0.5 inches, such as a range of 0.2 inches to 0.3 inches or a range of 0.22 inches to 0.25 inches.

In another example, the grip plate 1204 can extend a distance forward at region 1210. In an example, the distance forward is in a range of 0.6 inches to 1 inch, such as a range of 0.65 inches to 0.9 inches or a range of 0.7 inches to 0.8 inches. In a further example, the height between an upper surface of the grip plate 1204 and an upper ridge 1222 of the post plate 1202 at the rear surface 1532 can be in a range of 0.25 inches to 0.3 inches, such as a range of 0.255 inches to 0.28 inches or even a range of 0.26 to 0.27 inches. The distance between the lower ridge 1212 and a lower surface of the grip plate 1204 at the rearward surface 1532 can have similar measurements.

Figure 17:
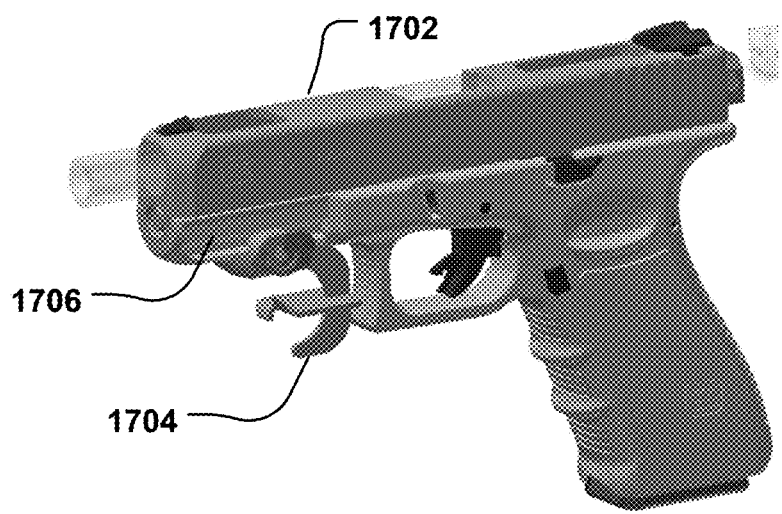
FIG. 17, FIG. 18, FIG. 19, and FIG. 20 include illustrations of an example adapter for a handgun.

In particular examples, the adapter can be formed for use with a smaller weapon or tool, such as a pistol. As illustrated in FIG. 17, FIG. 18, FIG. 19, and FIG. 20, the adapter can be configured for use with a handgun. For example, as illustrated in FIG. 17, handgun 1702 includes a rail system 1706 to which a hook adapter 1704 is attached.

Figure 18:
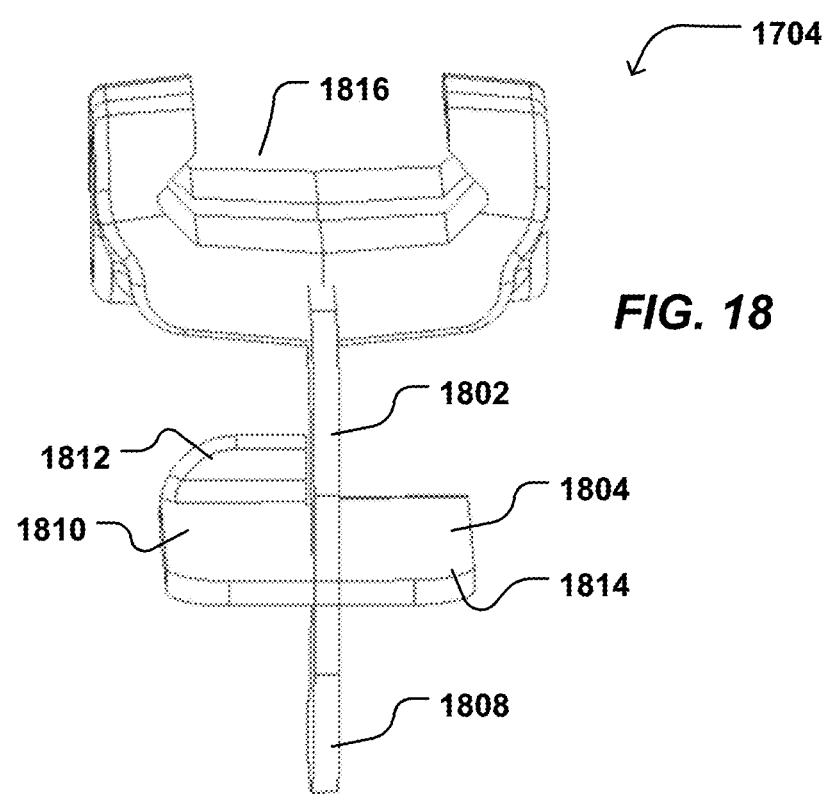

As illustrated in FIG. 18, the hook adapter 1704 includes a vertical plate or shaft 1802 and a horizontal plate 1804. The horizontal plate 1804 includes side extensions 1810 and 1814. Further, the horizontal plate 1804 includes a forward lip 1812 extending upward and a second lip 1818 extending downward.

Figure 19:
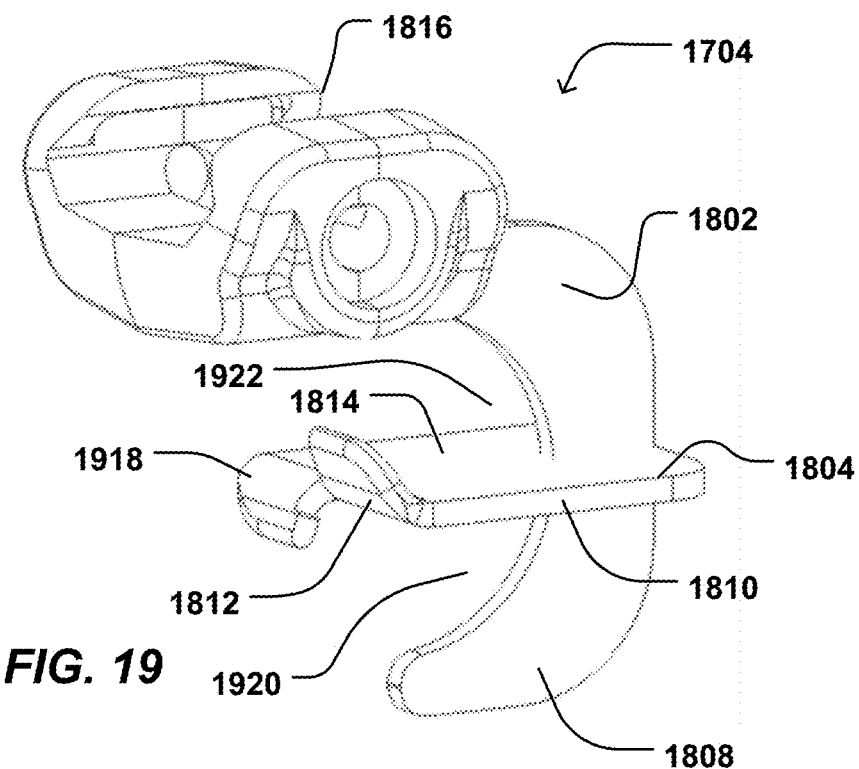
Figure 20:
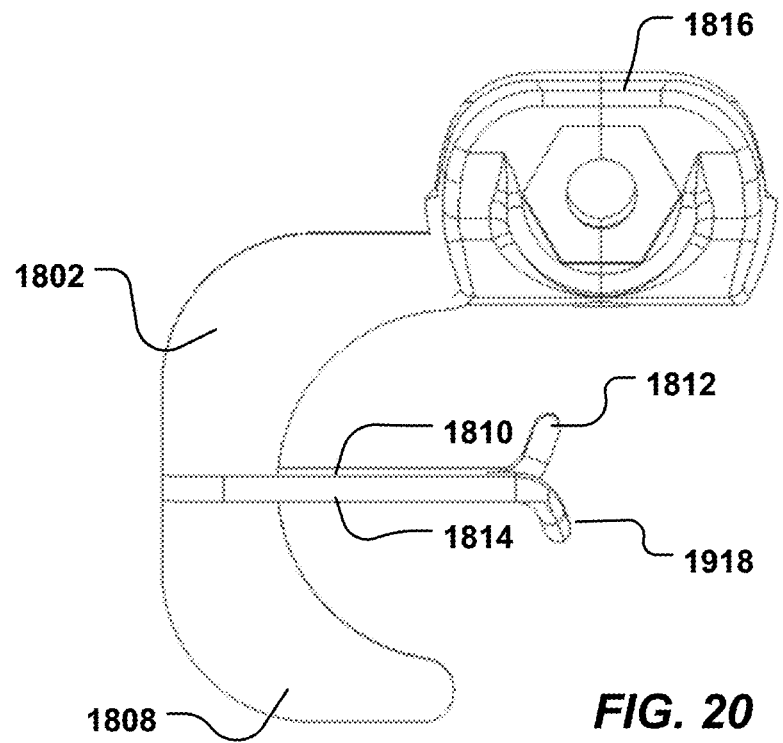
Figure 21:
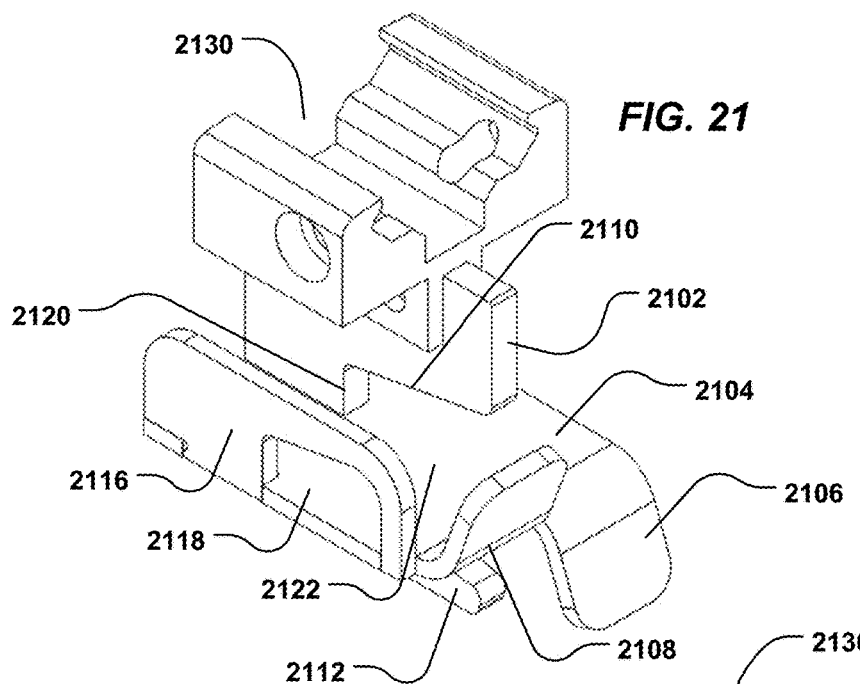
FIG. 21, FIG. 22, FIG. 23, FIG. 24, FIG. 25 and FIG. 26 include illustrations of a further example adapter for a handgun.
Figure 22:
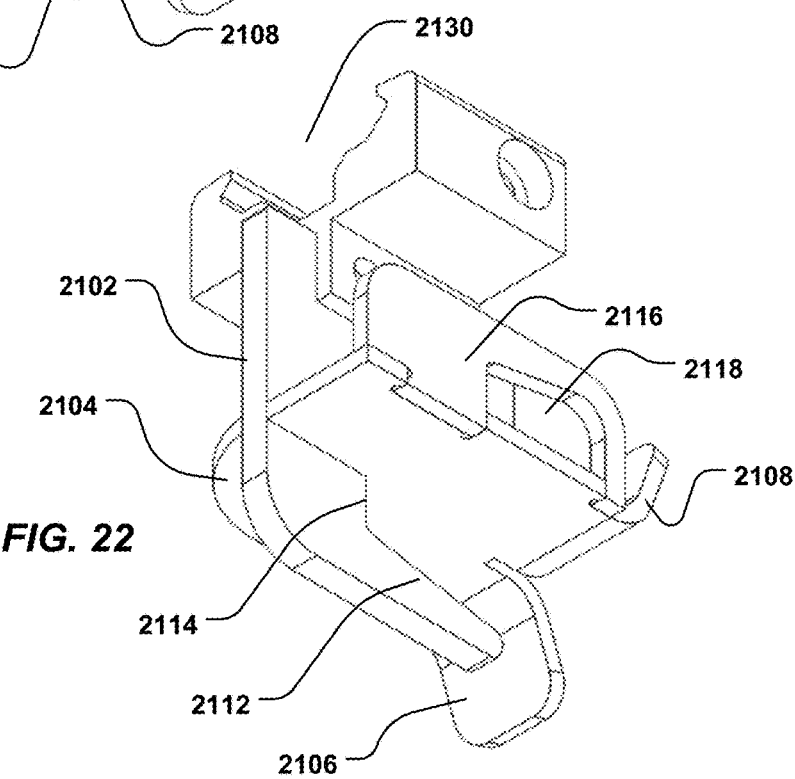
Figure 23:
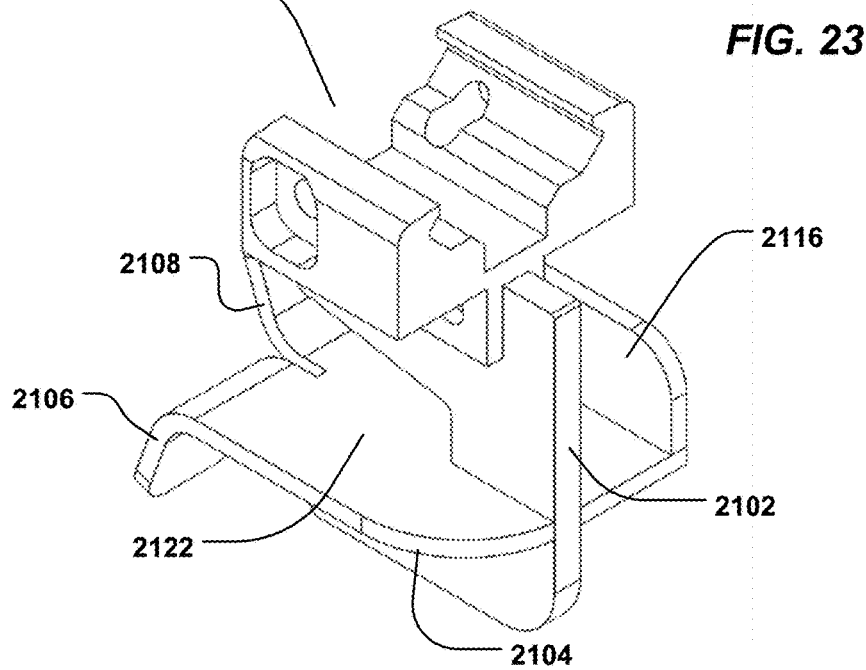

As illustrated in FIG. 19, the vertical plate or shaft can further extend downward to a curved portion 1808 that defines a cavity or opening 1920 below the horizontal plate 1804 and the second cavity 1922 above the horizontal plate 1804. The hook can reach around the central shaft having the curved portion extending the cross the central shaft 1802 in through cavities 1922 and 1920. Straight portions of the hook extend backwards and when closed secure the hook to the horizontal plate 1804. The hook when closed is prevented from moving forward by the lips 1812 and 1918.

The central shaft 1802 and or the horizontal plate 1804 can be formed of metal plate materials. Optionally, the metal plate materials can be coated with an elastomeric material to further prevent slippage of the hook when attached to the adapter.

A further example is illustrated in FIG. 21, FIG. 22, FIG. 23, FIG. 24, FIG. 25, and FIG. 26. The post plate 2102 is connected to a grip plate 2104. For example, the post plate 2102 can be coupled to the grip plate 2104 in an approximately perpendicular fashion. An equipment interface or connector 2130 can be coupled with the post plate 2102, for example, at the end of the post plate 2102 distal from the grip plate 2104. The post plate 2102 can be formed of material such as sheet material, as described above. Alternatively, the post plate 2102 can be formed of a rod or other material. Similarly, the grip plate 2104 can be formed of sheet material similar to those described above.

The post plate 2102 can include a concave surface 2120 defines an upper ridge 2110 extending over an upper surface of the grip plate 2104 and a lower ridge 2112 extending under a lower surface of the grip plate 2104. The grip plate 2104 can extend at 2122 from the concave surface 2120 of the post plate 2102. One or more lips 2106 or 2108 can be defined at an end of the grip plate 2104 distal from the concave surface 2120 of the post plate 2102. For example, a lip 2108 can extend out of the plane defined by the grip plate 2104 in an upward direction. Another lip 2106 can extend in a different direction, such as a downward direction out of the plane defined by the grip plate 2104. The grip plate 2104 can further define a loop 2116 at an edge of the grip plate 2104. For example, the loop 2116 can define an opening 2118. The loop 2116 can be located in an edge of the grip plate 2104 distal from the post plate 2102 and parallel to the post plate 2102.

Figure 24:
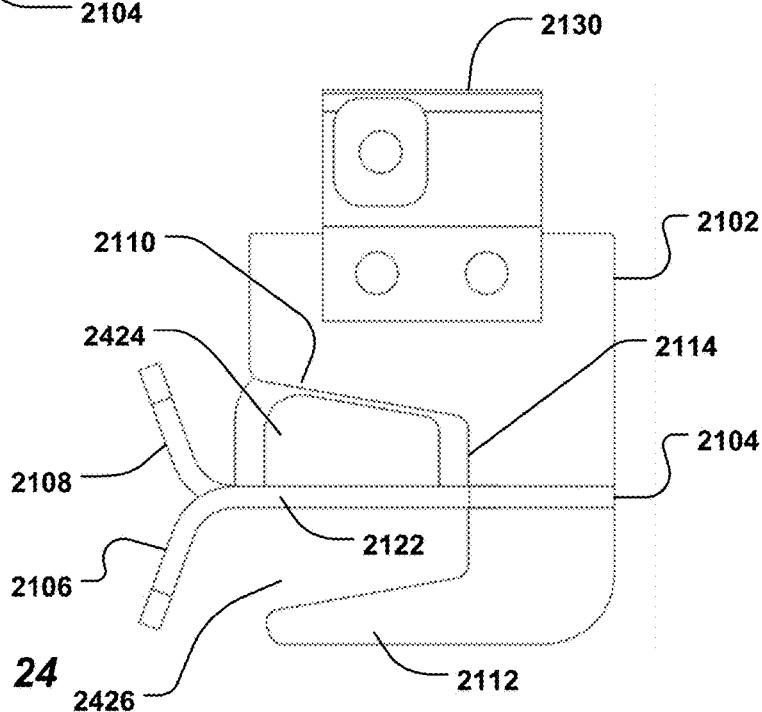

Turning to FIG. 24, in practice, when engaging a Hosmer-like hook, such as a Hosmer 5 or Hosmer 7 prosthetic hook, the hook can engage the adapter from the side opposite the loop 2116. For example, an upper portion or finger of the hook can engage a top surface of the grip plate 2104 extending into the cavity 2424 defined between an upper ridge 2110 of the concave surface 2114 and an upper surface of the grip plate 2104. Another finger of the hook can enter the cavity 2426 defined between a lower ridge 2112 of the post plate 2102 and the lower surface of the grip plate 2104. An end of a finger of the hook can extend around the post plate 2102 and engage the opening 2118 of the loop 2116.

In particular, the upper ridge 2110 of the concave surface 2114 can engage a rearward portion of the concave surface at angles such as those described above in relation to FIG. 15. Similarly, the lower ridge 2112 can engage a rearward surface of the concave surface 2114 at angles as described above in relation to FIG. 15.

An opening to the cavity 2424 defined between the lip 2108 and a closest point of the post plate 2102 can have a width in a range of 0.25 inches to 0.35 inches, such as a width in a range of 0.26 inches to 0.3 inches or a range of 0.275 inches to 0.285 inches. An opening defined into cavity 2426 between the lip 2106 and the closest surface of post plate 2102 can have a width in a range of 0.28 inches to 0.35 inches, such as width in a range of 0.3 inches to 0.35 inches or even 0.325 inches to 0.34 inches.

Figure 25:
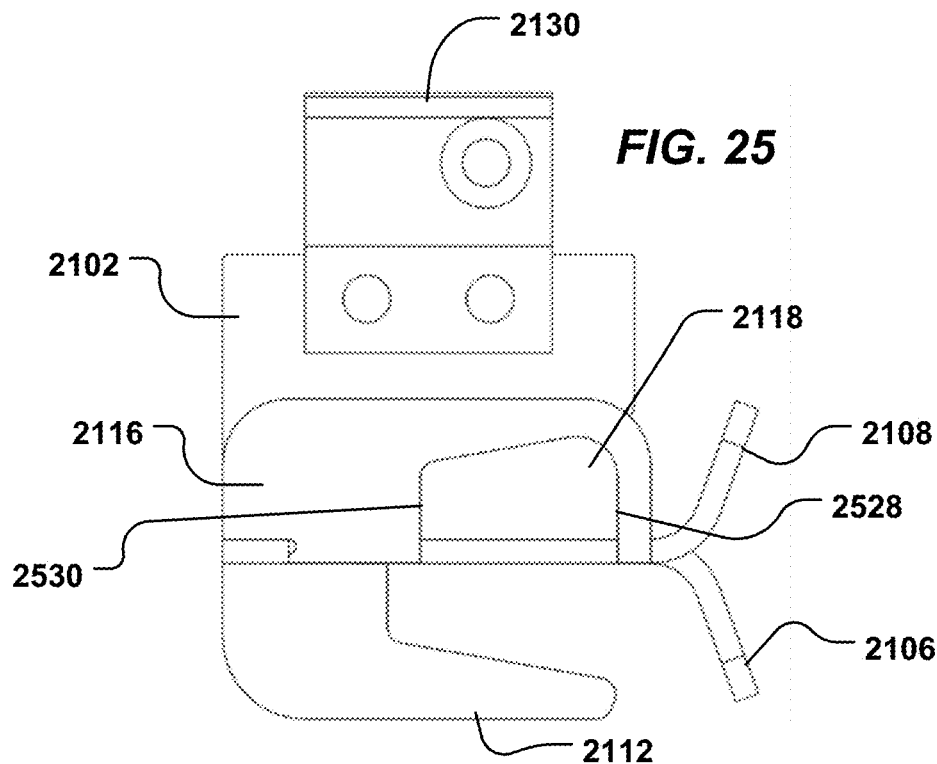
Figure 26:
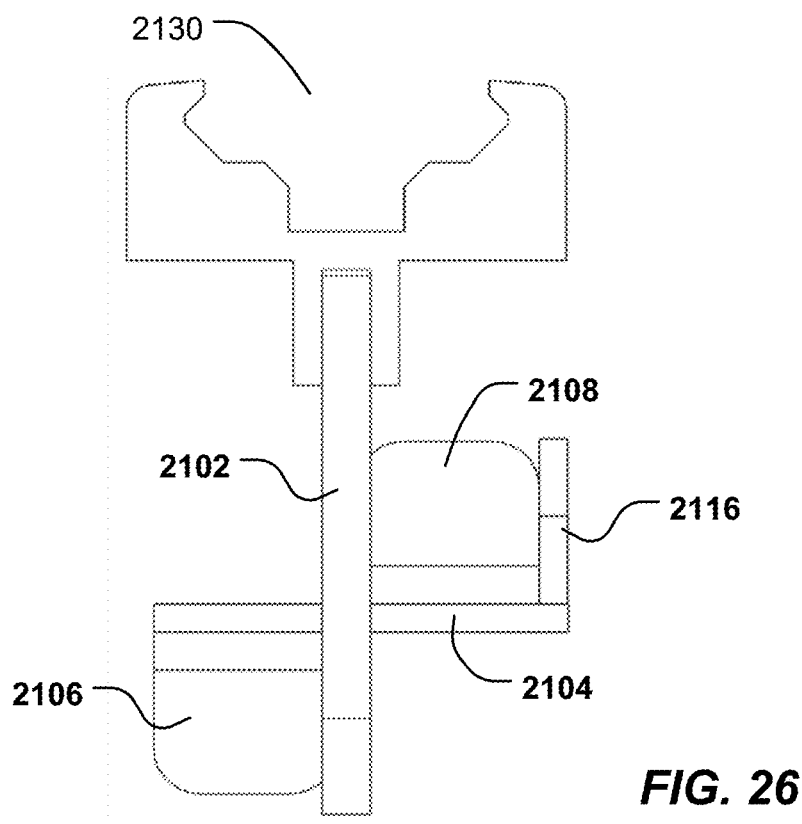

Turning to FIG. 25, the loop 2116 can define the opening 2118 to receive a tip of a finger of the Hosmer-like prosthetic hook. In particular, the opening 2118 can be tapered, being larger at a forward surface 2528 and shorter at a rearward surface 2530. For example, the opening at the forward surface 2528 can be in a range of 0.29 inches to 0.35 inches, such as a range of 0.3 inches to 0.33 inches or even a range of 0.3 inches to 0.32 inches. The rear surface 2530 of the opening 2118 can have a height in a range of 0.21 inches to 0.25 inches, such as a range of 0.22 inches to 0.24 inches or even a range of 0.23 inches to 0.24 inches.

In practice, as the Hosmer-like hook engages the adapter, it wraps around the post plate 2102 and has a tip of the upper finger enter into the opening 2118, the hook is drawn rearward and is pinched both by the height between the post plate 2102 and the grip plate 2104, as well as being secured and pinched by the restricted height of the opening 2118.

In a first aspect, a prosthetic adaptor includes a post plate, a grip plate coupled to the post plate, and an equipment interface coupled to the post plate.

In an example of the first aspect, the equipment interface is coupled to the post plate at an end of the post plate distal from the grip plate.

In another example of the first aspect and the above examples, the equipment interface is a Picatinny interface, or an m-lock interface.

In a further example of the first aspect and the above examples, the post plate includes a concave surface. For example, the concave surface is configured to receive a Hosmer-like prosthetic hook. In another example, the concave surface is to pinch a finger of the hook when the hook is drawn toward the post plate along the grip plate. In an additional example, the grip plate extends forward from the concave surface. In a further example, a top cavity is formed between a top surface of the grip plate and the concave surface of the post plate. For example, the top cavity is configured to receive a finger of a Hosmer-like prosthetic hook. In another example, a bottom cavity is formed between a bottom surface of the grip plate and the concave surface of the post plate. For example, the bottom cavity is configured to receive a second finger of the Hosmer-like prosthetic hook.

In an additional example of the first aspect and the above examples, the grip plate is coupled to the post plate approximately perpendicular to the post plate.

In another example of the first aspect and the above examples, the grip plate includes a lip at an edge distal from the post plate. For example, the edge is a front edge. In another example, the lip extends in a first direction out of a plane of the grip plate. For example, the grip plate further includes a second lip at the edge of the grip plate and extending in a second direction out of the plane of the grip plate.

In a further example of the first aspect and the above examples, the grip plate further includes a loop at an edge of the grip plate. For example, the loop the edge is a side edge of the grip plate distal from the post plate. In another example, the loop is configured to receive a tip portion of a Hosmer-like prosthetic hook. In a further example, the loop defines a taller opening toward a front of the grip plate than toward a rear of the grip plate.

In an additional example of the first aspect and the above examples, the grip plate extends further around the post plate at a first side than at a second side. For example, the grip plate extends rearward beyond the post plate on the first side.

In a second aspect, an adapted device includes a firearm and an adapter coupled to the firearm and configured to receive a Hosmer-like prosthetic hook.

In an example of the second aspect, the adapted device further includes a barrel and handguard, the adapter coupled to the firearm at the handguard.

In another example of the second aspect, the adapted device further includes a barrel and frame, the adapter coupled to the firearm at the frame.

In a further example of the second aspect and the above examples, the adapter further includes a post plate, a grip plate coupled to the post plate, and an equipment interface coupled to the post plate.

In an example of the second aspect and the above examples, the equipment interface is coupled to the post plate at an end of the post plate distal from the grip plate.

In another example of the second aspect and the above examples, the equipment interface is a Picatinny interface, or an m-lock interface.

In a further example of the second aspect and the above examples, the post plate includes a concave surface. For example, the concave surface is configured to receive a Hosmer-like prosthetic hook. In another example, the concave surface is to pinch a finger of the hook when the hook is drawn toward the post plate along the grip plate. In an additional example, the grip plate extends forward from the concave surface. In a further example, a top cavity is formed between a top surface of the grip plate and the concave surface of the post plate. For example, the top cavity is configured to receive a finger of a Hosmer-like prosthetic hook. In another example, a bottom cavity is formed between a bottom surface of the grip plate and the concave surface of the post plate. For example, the bottom cavity is configured to receive a second finger of the Hosmer-like prosthetic hook.

In an additional example of the second aspect and the above examples, the grip plate is coupled to the post plate approximately perpendicular to the post plate.

In another example of the second aspect and the above examples, the grip plate includes a lip at an edge distal from the post plate. For example, the edge is a front edge. In another example, the lip extends in a first direction out of a plane of the grip plate. For example, the grip plate further includes a second lip at the edge of the grip plate and extending in a second direction out of the plane of the grip plate.

In a further example of the second aspect and the above examples, the grip plate further includes a loop at an edge of the grip plate. For example, the loop the edge is a side edge of the grip plate distal from the post plate. In another example, the loop is configured to receive a tip portion of a Hosmer-like prosthetic hook. In a further example, the loop defines a taller opening toward a front of the grip plate than toward a rear of the grip plate.

In an additional example of the second aspect and the above examples, the grip plate extends further around the post plate at a first side than at a second side. For example, the grip plate extends rearward beyond the post plate on the first side.

In a third aspect, a method of adapting a firearm for use with a prosthetic hook includes coupling an adapter to the firearm, the adapter configured to receive a Hosmer-like hook and engaging the adapter with the Hosmer-like hook by a wearer of the Hosmer-like hook.

While the adapters illustrated herein relate to adaptations to firearms, one of ordinary skill could envision based on the disclosure herein adaptations to other sporting equipment such as bats rackets, weightlifting equipment, ball adapters, and surfaces for use in ball control such as baseballs, basketballs, footballs, tennis balls, golf balls, golf clubs, or any combination thereof.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A prosthetic adaptor comprising:
    a post plate having a concave surface defining an upper ridge and a lower ridge;
    a grip plate coupled approximately perpendicular to the post plate and disposed between the upper ridge and the lower ridge at the concave surface defining a top cavity between the grip plate and the upper ridge and a bottom cavity between the grip plate and the lower ridge, the grip plate extending out from the concave surface of the post plate and around a first side of the post plate; and
    an equipment interface coupled to the post plate.

2. The prosthetic adapter of claim 1, wherein the equipment interface is coupled to the post plate at an end of the post plate distal from the grip plate.

3. The prosthetic adapter of claim 1, wherein the equipment interface is a Picatinny interface, or an M Lok interface.

4. The prosthetic adapter of claim 1, wherein the concave surface is configured to receive a Hosmer-like prosthetic hook.

5. The prosthetic adapter of claim 1, wherein the concave surface is to pinch a finger of the hook when the hook is drawn toward the post plate along the grip plate.

6. The prosthetic adapter of claim 1, wherein the top cavity is configured to receive a finger of a Hosmer-like prosthetic hook.

7. The prosthetic adapter of claim 6, wherein the bottom cavity is configured to receive a second finger of the Hosmer-like prosthetic hook.

8. The prosthetic adapter of claim 1, wherein the grip plate includes a lip at an edge distal from the post plate.

9. The prosthetic adapter of claim 8, wherein the edge is a front edge.

10. The prosthetic adapter of claim 8, wherein the lip extends in a first direction out of a plane of the grip plate.

11. The prosthetic adapter of claim 10, wherein the grip plate further includes a second lip at the edge of the grip plate and extending in a second direction out of the plane of the grip plate.

12. The prosthetic adapter of claim 1, wherein the grip plate further includes a loop at an edge of the grip plate.

13. The prosthetic adapter of claim 12, wherein the edge is a side edge of the grip plate distal from the post plate.

14. The prosthetic adapter of claim 12, wherein the loop is configured to receive a tip portion of a Hosmer-like prosthetic hook.

15. The prosthetic adapter of claim 12, wherein the loop defines an opening that is taller toward a front of the grip plate than toward a rear of the grip plate.

16. The prosthetic adapter of claim 12, wherein the loop extends parallel to the post plate.

17. The prosthetic adapter of claim 1, wherein the grip plate extends around a second side of the post plate.

18. The prosthetic adapter of claim 17, wherein the grip plate extends further around the post plate at the first side than at the second side.

19. The prosthetic adapter of claim 1, where the grip plate extends rearward beyond the post plate on the first side.

* * * * *